(12) United States Patent
Ehmann et al.

(10) Patent No.: US 8,563,701 B2
(45) Date of Patent: Oct. 22, 2013

(54) METHODS FOR REMOVAL OF MICROCYSTINS AND ISOLATION OF PHYCOCYANIN FROM CYANOBACTERIA

(75) Inventors: Axel Ehmann

METHODS FOR REMOVAL OF MICROCYSTINS AND ISOLATION OF PHYCOCYANIN FROM CYANOBACTERIA

CROSS REFERENCE TO RELATED APPLICATIONS

This is the U.S. National Stage of International Application No. PCT/US2010/040537, filed Jun. 30, 2010, which was published in English under PCT Article 21(2), which in turn claims the benefit of U.S. Provisional Application No. 61/271,315, filed Jul. 20, 2009, which is incorporated by reference herein in its entirety.

FIELD OF THE DISCLOSURE

This disclosure relates to methods of removing contaminating microcystins toxins from preparations of blue-green algae. It also relates to methods of purifying phycocyanin from blue-green algae extracts.

BACKGROUND

The health benefits of a diet including blue-green algae such as *Aphanizomenon flos aquae* (AFA) and species of *Arthrospira* (commonly known as *Spirulina*) have long been appreciated. In particular, certain phytochemicals such as phycocyanin are well known for beneficial properties including antioxidant and anti-inflammatory capabilities (Shih et al., *Anesthesia & Analgesia*, 108:1303-1310, 2009). However, accessing these benefits in a safe and economical way continues to be a challenge.

Blooms of harmful *Microcystis aeruginosa*, which produce toxic microcystins, are found world-wide in bodies of fresh and low salinity water that also serve as the natural sources of beneficial blue-green algae. One such contaminated body of water is the Klamath Lake, the only commercial source of AFA in the world. Although methods of removing *Microcystis* from mixtures of other algae such as of AFA have been developed, such methods do not remove any microcystins that may already be present in the water. Similarly, although several methods have been employed to purify phycocyanin, it remains a challenge to produce large-scale, readily ingestible quantities of this beneficial protein.

Thus a need exists for methods of processing blue-green algae to remove harmful microcystins toxins and isolate beneficial phycocyanin.

SUMMARY OF THE DISCLOSURE

Described herein are methods of removing microcystins contamination from a contaminated aqueous extract of bluegreen algae. These methods comprise contacting a microcystins-contaminated aqueous extract of blue-green algae with a non-ionic macroreticular adsorbent resin, whereby microcystins adsorb to the resin to produce a microcystins-free extract; and collecting the microcystins-free extract.

Also described herein are methods of purifying a bluegreen algae composition. These methods comprise freezing a blue-green algae composition suspected of microcystins contamination to produce a frozen preparation; thawing the frozen preparation, thereby lysing the algae cells to produce a lysed preparation; removing suspended solids from the lysed preparation to produce an extract; contacting the extract with a non-ionic macroreticular adsorbent resin, whereby microcystins adsorb to the resin to produce a purified blue-green algae extract; and collecting the purified blue-green algae extract.

Additionally described herein are methods of isolating phycocyanin from blue-green algae. These methods comprise suspending dried, fresh or frozen blue-green algae in an aqueous solution to produce a cell suspension; disrupting the integrity of the blue-green algae cells, thereby releasing cytoplasmic contents, to produce a disrupted cell suspension; separating solid and liquid phases of the disrupted cell suspension; contacting the liquid phase of the disrupted cell suspension with a non-ionic macroreticular adsorbent resin; collecting the liquid phase from the resin to produce a phycocyanin extract; and optionally dehydrating the phycocyanin extract.

The foregoing and other objects, features, and advantages of the invention will become more apparent from the following detailed description, which proceeds with reference to the accompanying figures.

DETAILED DESCRIPTION

I. Abbreviations

AFA: *Aphanizomenon flos aquae*
ELISA: Enzyme-linked immunosorbent assay
MIC: Microcystins
ppb: Parts per billion
ppm: Parts per million
PC: Phycocyanin
RIA: Radioimmunoassay

II. Terms

The following explanations of terms and methods are provided to better describe the present methods, and to guide those of ordinary skill in the art in the practice of the present disclosure. It is also to be understood that the terminology used in the disclosure is for the purpose of describing particular embodiments and examples only and is not intended to be limiting.

Activated charcoal: A form of highly porous processed carbon. Also known as activated carbon or activated coal. Due to its porosity, activated charcoal has a large surface area available for adsorption of organic molecules.

Adsorption: The process by which a molecule from a substance, such as a liquid or gas, is attracted and adheres to an exposed solid surface that is in contact with the liquid or gas. For example, microcystins will adsorb to an adsorbent such as a non-ionic macroreticular resin such as an AMBERLITE® resin. Other exemplary adsorbents are silica gel and activated charcoal. Adsorbents are frequently used in liquid chromatography applications, and are loaded or "packed" into a column as a bed through which a solution to be fractionated is passed.

Adsorption capacity: The amount of material that may adsorb to a given adsorbent. The capacity of any given adsorbent is dependent on multiple factors including, but not limited to, the surface area of the adsorbent, adsorbent pore size, concentration of the adsorbate, and temperature.

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

Antibodies for use in the methods and devices of this disclosure can be monoclonal or polyclonal. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Antigen: A compound, composition, or substance that may be specifically bound by the products of specific humoral or cellular immunity, such as an antibody molecule or T-cell receptor. Antigens can be any type of biologic molecule including, for example, simple intermediary metabolites, sugars (e.g., oligosaccharides), lipids, and hormones as well as macromolecules such as complex carbohydrates (e.g., polysaccharides), phospholipids, nucleic acids and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens. In one example, an antigen is a microcystin toxin.

Aluminum oxide: Also known as alumina or activated alumina, a highly porous material with similar applicability as silica gel as a desiccant and adsorbent.

*Aphanizomenon floc aquae* (AFA): A species of blue-green algae naturally found in the Klamath Lake in Oregon in the United States. Under certain environmental conditions, *Microcystis* blooms mix with AFA and it is not possible to separate the two types of algae at the time of AFA harvest. Such mixtures of AFA and *Microcystis* are a microcystins-contaminated AFA preparation.

Aqueous: Water based solutions, such as water-only or buffered saline solutions.

Bed volume: An amount that is synonymous with column volume for a packed column.

Blue-green algae: Gram-negative photosynthetic bacteria belonging to Division Cyanophyta that may exist in unicellular, colonial, or filamentous forms. Representative blue-green algae include, but are not limited to, *Spirulina* (*Arthrospira*) species and *Aphanizomenon* species. *Aphanizomenon flos aquae* (AFA) is one specific, non-limiting type of blue-green algae.

The term "algae" is the plural form of "alga," which is a cell of a microalgae species. For example (and without limitation), "blue-green algae" refers to multiple cells of a single *Aphanizomenon* species, multiple cells of a single *Spirulina* (*Arthrospira*) species, or a mixture of cells from multiple *Aphanizomenon* and/or *Spirulina* (*Arthrospira*) species.

Component of blue-green algae: Any fraction, extract, or isolated or purified molecule from a blue-green algae cell. In one embodiment, the component (or molecule) is a protein or a glycoprotein or nucleic acid. In another embodiment, the component (or molecule) is a phytochemical. Thus, the blue-green algae are disrupted, an inorganic or organic solvent is added, and components (or molecules) are collected. Specific, non-limiting examples of components are isolated using high performance liquid chromatography, thin layer chromatography, affinity column, magnetic beads or distillation.

Extract. A concentrated preparation of a composition from an organism, such as a blue-green algae, or component thereof, obtained by removing active constituents of the composition with suitable solvents. In particular examples, an extract can be further concentrated by evaporating all or nearly all of the solvent, and adjusting the residual mass or powder to a pre-determined standard amount.

Flow rate: The rate at which a liquid moves through a packed column. The effluent flow rate is the flow rate as measured by the rate at which liquid flows out of a column.

Fraction: A fraction of an organism, such as a species of blue-green algae, is any isolated or purified molecule or complex of molecules. A fraction can be obtained by any method known to the art by which molecules are isolated or purified from a cell, such as by extraction or ultracentrifugation. In particular examples, a fraction is in liquid form. In other examples a fraction is in a solid form, such as a dried form. In still other examples, a fraction can be formulated as an inhalable particulate.

Isolated: An "isolated" biological component (such as a nucleic acid molecule, peptide, or cell) has been purified away from other biological components in a mixed sample (such as a cell extract). For example, an "isolated" peptide or nucleic acid molecule is a peptide or nucleic acid molecule that has been separated from the other components of a cell in which the peptide or nucleic acid molecule was present (such as an expression host cell for a recombinant peptide or nucleic acid molecule).

*Microcystis aeruginosa*: A common species of blue-green algae that blooms in fresh and low salinity water. *Microcystis* blooms are more frequently associated with warm, fresh, nutrient enriched water. Blooms generally occur in mid to late summer and can carry on into the fall. *Microcystis* blooms occur worldwide, including China, Brazil, Australia, the United States and much of Europe. Ingestion of concentrations of *Microcystis* is associated with gastrointestinal illness in humans and potentially lethal disease in animals. *Microcystis* also produces multiple toxins known as microcystins, which are associated with severe liver damage and cancer.

Microcystin: Cyclic nonribosomal peptides (independent of messenger RNA) produced by *Microcystis*. Microcystins strongly inhibit protein phosphatases type 1 (PP1) and 2A (PP2A) and can be very toxic for plants and animals including humans; particularly to the liver. Microcystins are composed of several uncommon amino acids such as dehydroalanine derivatives and the special β-amino acid ADDA ((all-S, all- E)-3-Amino-9-methoxy-2,6,8-trimethyl-10-phenyldeca-4,6-diene acid). Among the known types of microcystins is Microcystin-LR.

Optional or optionally: A phrase indicating that the subsequently described event or circumstance can but need not occur, and that the description includes instances where said event or circumstance occurs and instances where it does not.

Polypeptide: A polymer in which the monomers are amino acid residues that are joined together through amide bonds. When the amino acids are alpha-amino acids, either the L-optical isomer or the D-optical isomer can be used, the L-isomers being preferred. The term polypeptide or protein as used herein encompasses any amino acid sequence and includes modified sequences such as glycoproteins. The term polypeptide is specifically intended to cover naturally occurring proteins, as well as those that are recombinantly or synthetically produced.

The term polypeptide fragment refers to a portion of a polypeptide that exhibits at least one useful epitope. The phrase "functional fragment(s) of a polypeptide" refers to all fragments of a polypeptide that retain an activity, or a measurable portion of an activity, of the polypeptide from which the fragment is derived. Fragments, for example, can vary in size from a polypeptide fragment as small as an epitope capable of binding an antibody molecule to a large polypeptide capable of participating in the characteristic induction or programming of phenotypic changes within a cell. An epitope is a region of a polypeptide capable of binding an immunoglobulin generated in response to contact with an antigen. Thus, smaller peptides containing the biological activity of insulin, or conservative variants of the insulin, are thus included as being of use.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

In some circumstances, variations in the cDNA sequence that result in amino acid changes, whether conservative or not, are minimized in order to preserve the functional and immunologic identity of the encoded protein. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80%, 90%, or even 95% or 98% identical to the native amino acid sequence. Programs and algorithms for determining percentage identity can be found at the NCBI website.

Purified: In a more pure form than is found in nature. The term purified does not require absolute purity; rather, it is intended as a relative term. A microcystins-free extract or preparation is one that has been purified of microcystins contamination. In one embodiment, a microcystins-free extract or preparation contains less than 5 parts per billion (ppb), more particularly less than 1 ppb, and most particularly less than 0.5 ppb. In another embodiment, a purified phycocyanin preparation is free of other non-blue organic compounds.

Silica gel: Solid, granular, and porous form of silica made from sodium silicate. It is a naturally occurring mineral that is purified and processed into either granular or beaded form. Often used as a desiccant Silica gel is also used in chromatography as a stationary phase of silica gel particles of 75-150 μm. Different particle sizes are used for achieving a desired separation of certain molecular sizes. Silica gel is polar, thus, non-polar components tend to elute before more polar ones. In some instances, hydrophobic groups (such as $C_{18}$ groups) are attached to the silica gel. In such examples, polar molecules elute first from the column, followed by polar molecules.

*Spirulina*: The common name for blue green algae of the genus *Arthrospira*. When used in dietary supplements, *Spirulina* is often a combination of, but is not limited to, two particular *Arthrospira* species: *Arthrospira platensis*, and *Arthrospira maxima*

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

The health benefits of a diet including blue green algae or components thereof have long been recognized. However, conveying such benefits safely and economically poses a continuing challenge. To that end, disclosed herein are methods of using non-ionic macroreticular adsorbent resins to remove microcystins toxins from a blue-green algae preparation. These resins are also useful to isolate phycocyanin from a blue-green algae extract. The large adsorption capacity of these resins make them ideal for producing commercial quantities of microcystins-free blue-green algae preparations and isolated phycocyanin.

Disclosed herein are methods of removing microcystins contamination from a contaminated aqueous extract of blue-green algae, for example *Aphanizomenon flos aquae*, comprising contacting a microcystins-contaminated aqueous extract of blue-green algae with a non-ionic macroreticular adsorbent resin, whereby microcystins adsorb to the resin to produce a microcystins-free extract; and collecting the microcystins-free extract. In particular examples, the resin is packed into a column. In such examples, contacting the contaminated aqueous extract of blue-green algae with the column consists of a single pass of a predetermined volume of contaminated aqueous extract through the column. In some examples, the column has an adsorption capacity for microcystins of 100-200, more particularly 150-200 bed volumes. In other examples, the column has a diameter to height ratio of one to five, more particularly one to three. In still further examples, the contaminated aqueous extract of blue-green algae is introduced into the column at an effluent flow rate of 0.1 to 2.0 liters per minute. In other examples, the contaminated aqueous extract of blue-green algae is filtered prior to contacting with the resin, for example in a filter with a pore size of five to ten micrometers. In yet further examples, the concentration of microcystins in the microcystins-free extract is detected following removal of microcystins. Still further examples comprise forming a powder from the collected extract.

Also disclosed herein are methods of purifying a blue-green algae composition comprising freezing a blue-green algae composition suspected of microcystins contamination to produce a frozen preparation; thawing the frozen preparation, thereby lysing the algae cells to produce a lysed preparation; removing suspended solids from the lysed preparation to produce an extract; contacting the extract with a non-ionic macroreticular adsorbent resin; and collecting the purified blue-green algae extract. In particular examples, the blue-green algae is freshly harvested. In other examples, it is resuspended dried blue-green algae. In some examples, removing suspended solids from the lysed preparation comprises filtering or centrifuging the lysed preparation and collecting the liquid phase. In still other examples, the blue-green algae is *Aphanizomenon flos aquae*.

Also disclosed herein are methods of isolating phycocyanin from blue-green algae comprising suspending dried, fresh or frozen blue-green algae in an aqueous solution to produce a cell suspension; disrupting the integrity of the blue-green algae cells, thereby releasing cytoplasmic contents, to produce a disrupted cell suspension; separating solid and liquid phases of the disrupted cell suspension; contacting the liquid phase of the disrupted cell suspension with a non-ionic macroreticular adsorbent resin; collecting the liquid phase from the resin to produce a phycocyanin extract; and optionally dehydrating the phycocyanin extract. Particular examples further comprise contacting the phycocyanin extract with a bed of silica gel (100-200 mesh); collecting the liquid phase from the silica gel to produce a second phycocyanin extract and optionally dehydrating the second phycocyanin extract. Other examples further comprise contacting the second phycocyanin extract with a bed of aluminum oxide; (acidic, Brockmann activated); collecting the liquid phase from the aluminum oxide to produce a third phycocyanin extract; and optionally dehydrating the third phycocyanin extract. Still other examples further comprise contacting the third phycocyanin extract with a bed of activated charcoal; collecting the liquid phase to produce a fourth phycocyanin extract; and optionally dehydrating the fourth phycocyanin extract.

In particular examples of the methods of isolating phycocyanin, the resin is packed into a column and contacting the liquid phase of the disrupted cell suspension comprises passing the liquid phase of the disrupted cell suspension through the column. In some examples, the column has an adsorption capacity of 1-10 bed volumes. In further examples, disrupting the integrity of the blue-green algae cells comprises homogenizing, sonicating or freezing and thawing the cells. In still further examples, separating solid and liquid phases of the disrupted cell suspension comprises filtering or centrifuging the disrupted cell suspension and collecting the liquid phase. In still further examples, the blue-green algae are *Aphanizomenon flos aquae* or a species of *Spirulina* (*Arthrospira*).

IV. Blue Green Algae Harvest and Preparation

The starting material for the methods disclosed herein is blue-green algae. Processes for growing, harvesting, and concentrating blue-green algae cells are known to the art. Blue-green algae, such as AFA or *Spirulina* (*Arthrospira*), can be isolated from any source. The source can be a natural source of blue-green algae, such as a lake (for example Klamath Lake). The source can also be a man-made source of blue-green algae such as an artificial lake or water source. The source can also be a bioreactor or fermentor. Additional sources can be environments produced to grow and harvest blue-green algae commercially.

The blue-green algae can be used directly in the disclosed methods, or can be stored as liquid, frozen liquid, dehydrated, freeze-dried, or dried using the method described below. In one embodiment, freshly harvested blue-green algae are collected into 250 gallon (approximately 950 liter) plastic totes, which are frozen for later use. In another embodiment, the blue-green algae are harvested and dried using DLT HYDRO•DRI™ Technology. The term "DLT HYDRO•DRI™ Technology," also known as REFRACTANCE WINDOW™ (RW) technology, refers to a system wherein the dryer utilizes the very properties of water to drive water out of the product. In brief, when water is placed over a heating source, heat gets dispersed in the water through convection. As it absorbs heat, water transmits infrared energy to the outside in three ways: evaporation, conduction, and radiation. If the surface of the water surface is covered by a transparent medium such as plastic, evaporation and its associated heat loss are blocked and only conduction occurs. The plastic membrane acts like a mirror reflecting infrared energy. When a moist material, such as wet blue-green algae is placed on the plastic surface, the water in the material creates a "window" that allows for the passage of infrared energy. It is believed that in this system the water in the material allows for radiation, conduction and evaporation all to occur, providing for exceptionally effective heat transfer. However after a few minutes, as the material dries, the infrared "window" closes and conduction remains the only means of heat transfer. Since plastic is a poor heat conductor, little heat is lost and transferred to the product. Therefore, when dried with DLT HYDRO•DRI™ Technology, algae are exposed to heat only briefly.

In this drying system, liquid algae (cells suspended in solution) are placed on the surface of the dryer's conveyor belt. The belt is a food grade mylar (transparent polyester film) set on the surface of hot water. Heat from the circulating water is conducted to the belt and then into the water present in the product to be dried, gently speeding the natural process of evaporation while protecting natural nutrients. As the product dries and water evaporates, heat ceases to be transmitted to the product. Without being bound by theory, this prevents the degradation of polypeptides, nucleic acids, nutrients and pigments. Thus, the drying process maintains algae temperature far below the temperature of the circulating water beneath the conveyor belt.

Other drying systems can be used to produce dried algae. Generally, three factors play a role in the degradation of algae: degree of heat, exposure to oxygen, and exposure time to heat. Applying a high amount of heat for a short period of time results in less degradation of the components of the blue-green algae. In one example, heat, such as a temperature of about 65° C. to about 80° C., is applied, such as a temperature of about 70° C. to about 75° C., or about 72° C. The heat can be applied for a sufficient amount of time to dry the algae, such as about 1 to about 15 minutes, or for about 2 to about 10 minutes, or for about 3 to about 7 minutes. In one example, heat is applied to the algae at 72° C. for only 3 to 5 minutes. This process is known to one of skill in the art, and is fully described at the Desert Lake Technology LLC website, and is described in Abonyi et al., "Evaluation of Energy Efficiency and Quality Retention for the REFRACTANCE WINDOW™ Drying System: Research Report, Washington State University, Pullman, Wash., Dec. 30, 1999). In addition to cells dried by DLT HYDRO•DRI™ Technology, freeze dried, vacuum dried, drum dried cells and spray-dried cells can also be utilized in the described methods.

V. Non-Ionic Macroreticular Adsorbent Resins

The methods disclosed herein provide novel uses for non-ionic macroreticular adsorbents well known in the art of liquid chromatography. Macroreticular ion exchange resins and their preparation are described throughout the art, for example in U.S. Pat. No. 4,224,415, issued Sep. 23, 1980, and U.S. Pat. No. 7,098,252, issued Aug. 29, 2006, both of which are incorporated herein by reference. Generally these synthetic polymeric adsorbents take the form of non-ionic macroreticular resins that adsorb and retain non-polar molecules through hydrophobic interactions, while polar molecules are retained less strongly. In particular examples, these adsorbents are usually employed under isocratic conditions (i.e., only a single eluent of fixed composition is used). As described herein, the methods of the present invention employ only water.

The adsorbent resins used in the current invention are usually made from a synthetic hydrophobic (e.g. polyvinylbenzene or polystyrene) resin that is synthesized from a monoethylenically unsaturated monomer and/or a polyethylenically unsaturated monomer. Examples of monoethylenically unsaturated monomers include styrene, vinyl pyridine, ethylvinylbenzene, and esters of (meth) acrylic acids. Examples of polyethylenically unsaturated monomers include divinylbenzene, trivinylbenzene, ethylene glycol, diacrylate, diallyl phthalate, trimethylolpropane trimethacrylate. In certain embodiments, the resins are polyaromatic resins.

The advantage of using these resins is that they have comparatively large surface areas (typically 450-900 $m^2/g$) and high porosity (pore volume, typically 0.6-1.8 ml/G) and large average pore sizes (typically 100 Å), which combined with a coarse particle size (typically 20-60 mesh, wet) allows for both high extract flow rates and large capacity for the retention of the impurities and toxins. These resins are manufactured under trade names such as DIAION™, AMBERLITE™ and DOWEX™, many of which are manufactured specifically for removal of undesirable molecules from food preparations. In particular examples, the adsorbent resin useful in the current invention includes, but is not limited to, AMBERLITE™ XAD16HP, AMBERLITE™ FPX66, DIAION™ PS-DVB or SEPABEADS™ SP70.

VI. Methods of Removing Microcystins

Blooms of the toxic *Microcystis* algae are a world-wide problem, and contaminate many fresh or low salinity water sources. In addition to contaminating potential sources of drinking water, *Microcystis* algae contaminate the waters of the Klamath Lake in Oregon, which is the only natural source of AFA in the world. The toxicity of the *Microcystis* algae is a result of the many microcystin toxins produced by the algae, such as microcystin LR. Thus, removing *Microcystis* from AFA is not sufficient to produce a microcystins-free preparation of AFA. Accordingly, microcystins toxins must be removed to produce safe preparations of AFA.

To that end, disclosed herein are methods of removing microcystins from a preparation of blue-green algae. The algae can be freshly-harvested, or it can be algae that was harvested and preserved for later use by any method known to the art. In particular examples, the algae been dehydrated as described herein, and then reconstituted in an aqueous solution. Because the resins described herein have an adsorption capacity for microcystins of 140 to 150 bed volumes, the total volume of an aqueous algae preparation, including algae extracts, that can be purified of microcystins contamination is potentially quite large, and is only limited by the amount of resin employed. Thus, in particular examples, commercial-scale quantities of an algae mixture (thousands of liters) can be processed simultaneously using one or more columns packed with the adsorbent resin described herein.

To effectively remove microcystins contamination from an algae preparation, it is necessary to lyse the algae cells, thereby releasing cytoplasmic contents (including microcystins) into the surrounding aqueous medium. The cells in the algae preparation can be lysed by any mechanical or chemical method known to the art including, but not limited to, homogenization, sonication, and freezing the preparation followed by thawing. Once the cytoplasmic contents of the suspended algae are released into the aqueous solution, cellular debris is removed by any method known to the art including centrifugation and filtration. The debris-free preparation (or supernatant, in those examples where the lysed algae suspension is centrifuged) is then ready for chromatographic separation by contact with an adsorbent resin described herein.

In particular examples of the described methods, a non-ionic macroreticular adsorbent resin of the type described above is packed into a column by methods known to the art. In particular examples, the column has a diameter to height ratio of 1:5. In other examples, the resin is packed into the column with a bed volume of 20 liters.

Following clearance of cellular debris, the aqueous algae preparation may still contain suspended solid particulates that can potentially impede passage of the algae preparation through the column. Thus, in particular examples, prior to contacting the aqueous algae preparation with the adsorbent resin, the aqueous algae preparation is passed through a filter with a pore size no smaller than 5-10 micrometers. In particular examples, the filter is fitted directly in front of a column packed with the adsorbent resin, so that the filtrate flows directly from the filter to the resin-containing column.

The aqueous algae preparation is contacted with the adsorbent resin by any method known to the art of chromatography. In particular examples, the aqueous algae preparation is applied to a column packed with the resin with a pump at an effluent flow rate of 0.1 to 2.0 liters per minute. In particular examples, the aqueous preparation is pumped onto the resin at an effluent flow rate at 0.4 liter per minute. The column effluent is then collected by any method known to the art.

In particular examples, the microcystin concentration of the effluent can be measured by any known method, such as the methods described below. In some examples, the microcystin-free effluent can be further processed to isolate a particular component(s) of the blue-green algae extract, such as the methods described herein of isolating phycocyanin or the methods of isolating low molecular weight components of blue-green algae described in International Patent Application No. PCT/US2010/029847, and which is incorporated herein by reference. In other examples, the microcystin-free effluent is formed into a powder by any known method of dehydration including, but not limited to DLT HYDRO•DRI™ Technology, freeze drying or spray drying.

One of skill in the art will appreciate that the described methods of removing microcystins from an aqueous extract are equally applicable to any microcystins-contaminated aqueous solution, such as a source of drinking water in which there are *Microcystis* blooms.

Microcystin Detection

Microcystins are detectable in a sample, for example a water sample or blue-green algae preparation, by any method known to the art of detecting peptides. Such methods include antibody-based immunoassays such as the enzyme-linked immunosorbant assay (ELISA) and radioimmunoassay (RIA).

By way of example, an ELISA is one type of immunoassay that can be used to determine the concentration of a microcystin such as microcystin-LR in a sample such as a sample of blue-green algae. A typical ELISA format involves a specific immobilized capture antibody, sample, a labeled detection antibody, chromogens, and stop solution. Antigen will bind to the immobilized capture antibody and thus can be detected with one or more antibodies. The antibody detection technique used with an ELISA may be direct or indirect. For direct antibody visualization of the microcystin peptide, anti-microcystin antibody is attached to a substrate, the substrate is incubated with a sample of blue-green algae, and the substrate is then incubated with another anti-microcystin antibody that has been enzyme-conjugated, for example an anti-microcystin antibody conjugated to alkaline phosphatase or horseradish peroxidase. For indirect antibody visualization of the microcystin peptide, anti-microcystin antibody is attached to the substrate, and the substrate is incubated with a sample of blue-green algae. The substrate is then incubated with an unconjugated microcystin-specific antibody (primary antibody), then with an enzyme-conjugated antibody (secondary antibody) that recognizes the primary antibody. Secondary antibodies for the indirect detection of primary antibodies are often conjugated with horseradish peroxidase or alkaline phosphatase. A substrate solution is then added, acted upon by the enzyme, and effects a color change. The intensity of the color change is proportional to the amount of antigen in the original sample. Primary and secondary antibodies also can be coupled to radioactive or fluorescent tags. The intensity of radioactive or fluorescent labeling is proportional to the amount of antigen present in the original sample.

In an alternative embodiment, microcystin can be assayed in a sample of blue-green algae by a competition immunoassay, such as a radioimmunoassay (RIA) utilizing microcystin standards labeled with a detectable substance, such as radiolabel, and an unlabeled antibody that specifically binds microcystin peptide. In this assay, the labeled microcystin standard is mixed with the microcystin-reactive antibody. Then, the sample of blue-green algae is combined with the antibody-bound labeled microcystin standards. The amount of unbound, labeled microcystin is then determined. The amount of microcystin in the sample of blue-green algae is proportional to the amount of unbound, labeled microcystin.

The concentration of microcystin detected is compared to a control, such as the concentration of microcystin in sample of blue-green algae harvested in *Microcystis*-free water. In other examples, the control is a standard value, such as a value that represents an average concentration of microcystin expected in a natural source of algae.

VII. Purification of Phycocyanin

Phycocyanin is a pigment protein from the light-harvesting phycobiliprotein family that is found in blue-green algae and provides the characteristic blue color of the algae. Phycocyanin is used as a natural food coloring for foods such as ice cream and is also known for having many beneficial properties as an antioxidant and anti-inflammatory agent, among others. However, until the current disclosure, large scale isolation of pure, readily-ingestible phycocyanin posed a major economic hurdle. All isolations and subsequent purification of PC to date have been carried out using classical buffer and precipitation based purification methods on an analytical scale. For this reason commercially available PC is extremely expensive.

Disclosed herein are methods of isolating phycocyanin from any blue-green algae, including, but not limited to AFA or a species of *Spirulina* (*Arthrospira*). The disclosed methods use the same types of non-ionic macroreticular adsorbents described for use in removing microcystins contamination of blue-green algae preparations, and provide a single-eluant method to isolate readily-ingestible phycocyanin. Purity of the various phycocyanin preparations disclosed herein is determined spectrophotometrically by measuring absorbance at 620 and 280 nanometer wavelengths. Purity of the preparations is indicated by an increase in the ratio of A620/A280. In particular examples the A620/A280 of the final isolated phycocyanin is less than or equal to 2, 3, or 4. In other examples the A620/A280 of the final isolated phycocyanin is greater than 4, such as 4.5 or even 5.

The blue-green algae for use in the disclosed methods of isolating phycocyanin may harvested and prepared as described above. Thus, freshly harvested as well as dried and reconstituted blue-green algae may be used in the disclosed methods.

In the methods disclosed herein, blue-green algae are suspended in water only. The integrity of the suspended algal cells is disrupted by any mechanical or chemical method of breaking open algal cells known to the art, including, but not limited to homogenization, sonication and freezing the algae suspension followed by thawing the suspension.

Suspended solid debris is removed from the liquid phase of the disrupted algae solution by standard methods including, but not limited to, filtration and/or centrifugation. Additional fine suspended particulate matter is removed by additional filtration.

Once the aqueous extract is cleared of solid particulates, it is brought into contact with a non-ionic polyaromatic macroreticular adsorbent such as those described above. As described above, exemplary adsorbents for use in the disclosed methods include, but are not limited to AMBERLITE™ XAS16HP, AMBERLITE™ FPX66, DIAION™ PS-DVB or SEPABEADS™ SP70.

In particular embodiments, the adsorbent is packed into any suitable column known to the art having a diameter to height ration greater than 1:3. In particular embodiments, phycocyanin is isolated from the majority of the non-blue organic components of the aqueous extract by a single passage over the resin-packed column, with the collected effluent containing the phycocyanin. In particular examples, one to ten bed volumes of aqueous extract are passed over the column, such as one bed volume, one and a half bed volumes or two bed volumes. The resultant phycocyanin containing effluent can then be used immediately, further purified, or dehydrated by any method known to the art including, but not limited to, DLT HYDRO•DRI™ Technology, freeze drying or spray drying. The dehydrated phycocyanin powder is stable in the dark at room temperature and is soluble in water.

The single pass of algae extract through the adsorbent resin will generally result in phycocyanin with an A620/A280 purity of less than or equal to 1.8. In particular examples, higher purity phycocyanin is describable. In such examples, the phycocyanin-containing extract is then passed over a bed of silica gel. Any silica gel known to the art may be used in this method, including silica gel with a 100-200 mesh. The resultant phycocyanin-containing effluent will typically have an A620/A280 purity of less than or equal to 2.8. This solution may be used immediately, further purified, or dehydrated to powder form as described. The dehydrated phycocyanin powder is stable in the dark at room temperature and is soluble in water.

In particular examples, phycocyanin of greater purity than 2.8 is desirable. In those examples, the effluent from the silica gel bed is passed over a bed of aluminum oxide (alumina). Any type of alumina known to the art may be used in the methods described herein. The resultant phycocyanin-containing effluent with typically have an A620/A280 purity of less than or equal to 3.5. This solution may be used immediately, further purified, or dehydrated to powder form as described. The dehydrated phycocyanin powder is stable in the dark at room temperature and is soluble in water.

In still further examples, phycocyanin of greater purity than 3.5 is desirable. In those examples the effluent from the alumina bed is passed over a bed of any type of activated charcoal known to the art. This step can be repeated multiple times with increasing A620/A280 purity of phycocyanin (4.0-5.0). However, total yield of phycocyanin decreases with each successive pass through the activated charcoal. The final purified phycocyanin-containing solution may be used immediately or dehydrated to powder form as described. The dehydrated phycocyanin powder is stable in the dark at room temperature and is soluble in water.

The optional purification steps (silica gel, alumina, and activated charcoal) may be performed in any order for removal of non-blue pigment organic molecules from the phycocyanin preparation. These purification steps may be carried out by any method known to the art of liquid chromatography. Thus, the solutions may be applied in any known manner to each adsorbent and the effluent may be collected in any known manner.

One of skill in the art will also appreciate that as disclosed herein, in addition to purifying phycocyanin, any contaminating microcystins that are in the starting algae suspension will be removed by contact with the non-ionic macroreticular adsorbent of the initial purification step. Thus, the phycocyanin that is produced by the disclosed methods is both free of unwanted organic impurities as well as harmful microcystins.

The following examples are provided to illustrate certain particular features and/or embodiments. These examples should not be construed to limit the invention to the particular features or embodiments described.

EXAMPLES

Example 1

Removal of Microcystins Contamination from a Blue-Green Algae Preparation

Figure 1:
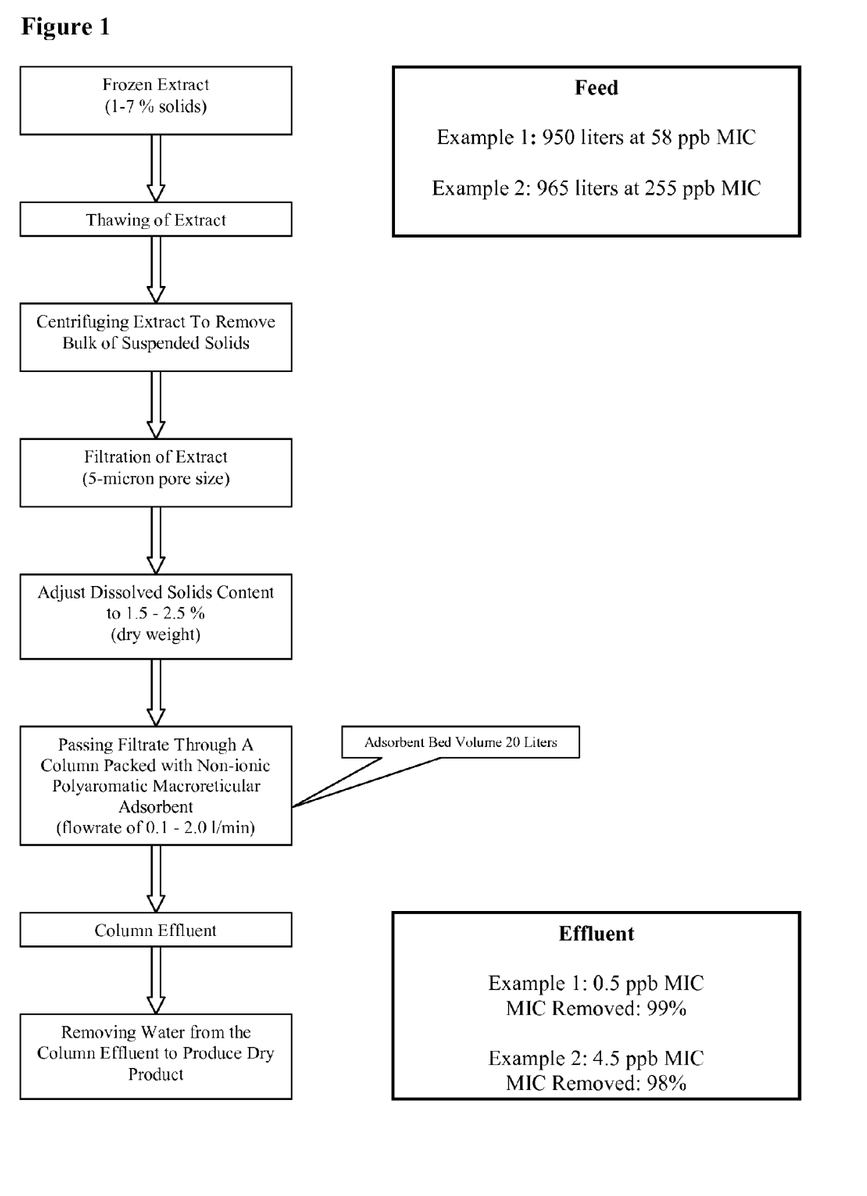
FIG. 1 is a process diagram illustrating one embodiment of the method of removal of microcystins (MIC) from contaminated aqueous extracts of *Aphanizomenon flos aquae*.

This example demonstrates the method of removing microcystins contamination from freshly-harvested AFA. This embodiment of the method is illustrated in FIG. 1.

1) AFA Preparation.

Freshly harvested AFA was collected in a 250 gallon plastic tote and frozen. The amount of algae collected was 1-5% dry weight, and was visibly contaminated with *Microcystis aeruginosa*. The contents of the tote were thawed to lyse the algal cells and release the water-soluble cellular constituents (such as phycocyanin and microcystin LR) into the aqueous extract. The suspended solids in the lysed cell mixture were removed by centrifugation, and the dissolved solid content of the supernatant was adjusted to 1.5-2.5% (dry weight) by either adding water or removing water by reverse osmosis.

2) Microcystin Removal.

AMBERLITE® FPX66 food grade adsorbent resin (Rohm and Hass) was packed into a column with a 20 liter bed volume and a column diameter to column height ratio of at least 1:5. The column was fitted with a 5 micron pre-column filter, and the microcystin-containing extract was pumped (in either up-flow or down-flow mode) once through the column at a column effluent flow rate of 0.4 liter per minute.

3) Microcystin Detection.

Microcystin was detected and quantified by ELISA using the EP022-1 QuantiPlate™ Kit for microcystin from ENVIROLOGIX™. In one experiment using this method, after cells were lysed and centrifuged, microcystins-LR concentration was 58 parts per billion in solution. Following the single pass through the column, 99.2% of the microcystins-LR was removed to a final concentration of 0.46 parts per billion in the column effluent. In another experiment, the contaminated solution contained 255 ppb microcystins-LR; of which 98% was removed by the disclosed method to a final concentration of 4.5 ppb in the column effluent.

Example 2

Scaled-Up Removal of Microcystins Contamination from a Blue-Green Algae Preparation This example illustrates a scaled-up method of removing microcystins contamination from a preparation of blue-green algae.

Removal of microcystins contamination from AFA can be scaled up to increase the amount of harvested cells that can be processed through a single column packed with a resin such as AMBERLITE FPX66. Cells are processed as in Example 1, except multiple plastic totes (for example, three) are processed simultaneously. Following removal of cellular debris, the supernatant of three totes is channeled into the column for microcystin removal. The post-column concentration of microcystins in the AFA preparation is measured by ELISA as in Example 2.

Example 3

Removal of Microcystins Contamination from Water

The presence of *Microcystis* algae in sources of drinking water, and the resultant contamination of those sources with microcystins, is a global public health problem. The methods disclosed herein of removing microcystins from a blue-green algae preparation can also be applied in the context of removing microcystins contamination from any contaminated aqueous solution, including sources of drinking water. This example illustrates the removal of microcystins contamination from any water sample.

Removal of microcystins from contaminated water was achieved by the same method described in Example 1, except that the water does not need to be frozen prior to processing. In examples where the water contains few suspended solids, it is also not necessary to centrifuge the sample to be purified. Using the method described in Example 1, two liters of microcystins-contaminated water containing 0.25 ppm microcystin LR were passed through a column with a 400 ml BV of FXP-66. The column effluent contained less than 0.16 ppb of microcystin LR.

Example 4

Water-Based Purification of Phycocyanin from a Blue-Green Algae Extract

Figure 2:
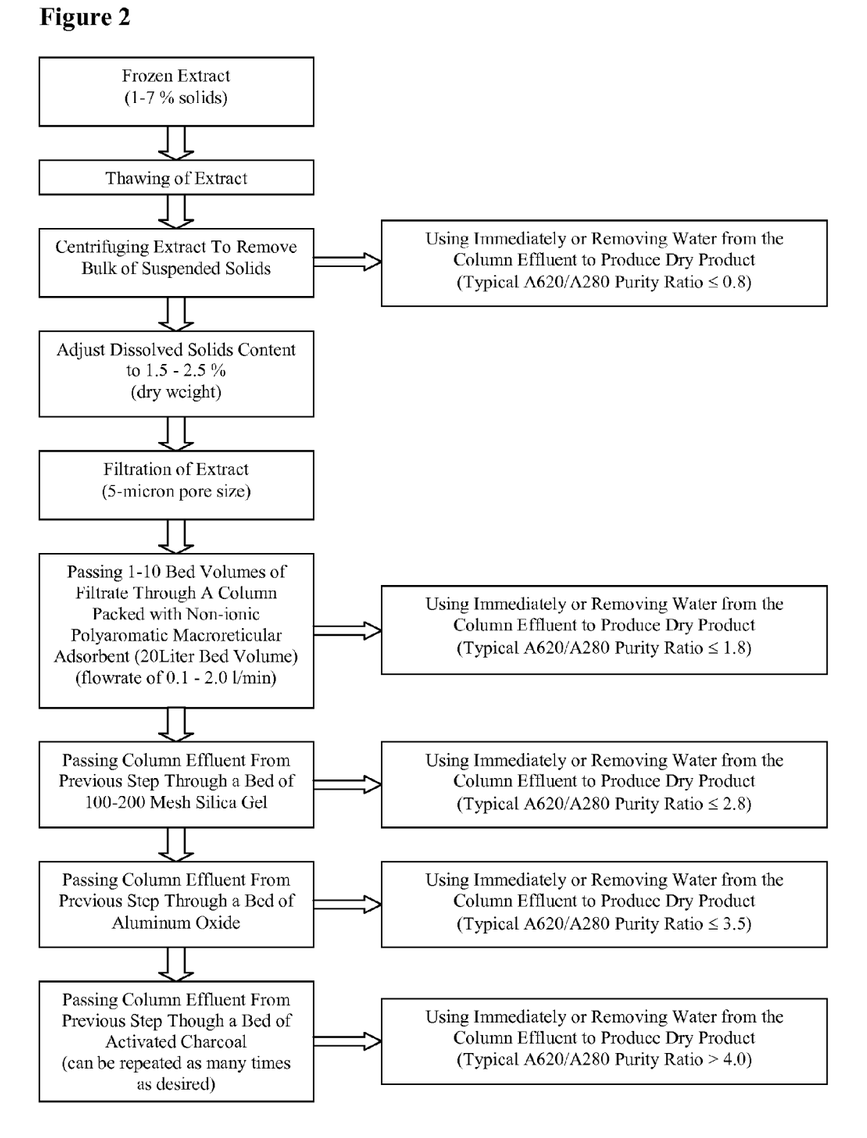
FIG. 2 is a process diagram illustrating one embodiment of the method for the purification of phycocyanin from aqueous extracts of cyanobacteria.

This example demonstrates the method of purifying phycocyanin from a *Spirulina* extract. This embodiment of the method is illustrated in FIG. 2.

Spray-dried *Spirulina* powder was resuspended in de-ionized water. The integrity of the algal cells was disrupted by high-speed or high-pressure homogenization. The water-insoluble cell debris was removed from the aqueous phase by high-speed centrifugation. The blue supernatant was collected and the phycocyanin purity was measured using a standard spectrophotometer. This first product, CR-PC, (Crude Phycocyanin) had an A620/A280<0.8.

The blue supernatant was passed through a low-, or high-pressure filtration with a pore size of 5 micrometer to remove any traces of suspended solids that would adversely affect the next step. The filtrate was passed through a resin bed of a polyaromatic macro-reticular non-ionic resin such as XAD-16HP or FPX66 (Rohm & Haas) to remove the bulk of the non-blue contaminants (this step removes on average 20-40% by weight of the non-pigmented organics). This second product, PU1-PC, (Purity1-Phycocyanin) had an A620/A280≤1.8). The purity of the phycocyanin in this second product is sufficient for many applications, however additional purification steps were used to further enhance the purity of the isolated phycocyanin.

In the first optional purification step, the PU1-PC was passed through a bed of silica gel, such as Silica 100-200 mesh to remove additional non-blue organic contaminants. This third product, PU2-PC, (Purity2-Phycocyanin) had an A620/A280≤2.8).

In the next optional purification step, the PU2-PC was passed through a bed of $Al_2O_3$ (acidic Brockmann activated Aluminum Oxide) to remove additional non-blue organic contaminants. This fourth product, PU3-PC, (Purity3-Phycocyanin) had an A620/A280≤3.5).

In the last optional purification step, the PU3-PC was passed through a bed of activated charcoal to remove the remaining traces of organic impurities. This fifth product, PU4-PC, (Purity4-Phycocyanin) had an A620/A280>4.0. Phycocyanin purities of greater than 4.5 or 5.0 were obtained at the expense of significant losses of phycocyanin yield by repeated passes over the bed of activated charcoal.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of isolating phycocyanin from blue-green algae comprising:
   suspending dried, fresh or frozen blue-green algae in a medium consisting of water to produce a cell suspension;
   disrupting the integrity of the blue-green algae cells in the medium, thereby releasing cytoplasmic contents into the medium, to produce a disrupted cell suspension; separating solid and a first soluble phases of the disrupted cell suspension;
   contacting the first soluble phase of the disrupted cell suspension with a non-ionic polyaromatic macroreticular adsorbent resin having a surface area of 450 to 900 meters $(m)^2$/gram(g);
   collecting a second soluble phase from the resin to produce a phycocyanin extract comprising less than 5 parts per billion (ppb) microcystins; and optionally dehydrating the phycocyanin extract.

2. The method of claim 1, further comprising contacting the phycocyanin extract with a bed of silica gel; collecting a third soluble phase phycocyanin from the silica gel; and optionally dehydrating the third soluble phase phycocyanin.

3. The method of claim 2, further comprising contacting the third soluble phase phycocyanin with a bed of aluminum oxide; collecting a fourth soluble phase phycocyanin from the aluminum oxide; and optionally dehydrating the fourth soluble phase phycocyanin.

4. The method of claim 3, further comprising contacting the fourth soluble phase phycocyanin with a bed of activated charcoal; collecting a fifth soluble phase phycocyanin; and optionally dehydrating the fifth soluble phase phycocyanin.

5. The method of claim 1, wherein the resin is packed into a column and wherein contacting the first soluble phase of the disrupted cell suspension comprises passing the first soluble phase of the disrupted cell suspension through the column.

6. The method of claim 5, wherein the column has an adsorption capacity of 1-10 bed volumes.

7. The method of claim 1, wherein disrupting the integrity of the blue-green algae cells comprises homogenizing, sonicating or freezing and thawing the cells.

8. The method of claim 1, wherein separating solid and first soluble phases of the disrupted cell suspension comprises filtering or centrifuging the disrupted cell suspension and collecting the first soluble phase.

9. The method of claim 1, wherein the blue-green algae is *Aphanizomenon flos aquae* or a species of *Spirulina*.

10. The method of claim 1, wherein said resin comprises a pore volume of 0.6 to 1.8 milliliters per gram.

11. The method of claim 1, wherein said second soluble phycocyanin extract contains less than 1 part per billion (ppb) microcystins.

12. The method of claim 1, wherein the water is deionized water.

* * * * *